US012799046B2

(12) United States Patent
Azam et al.

(10) Patent No.: US 12,799,046 B2
(45) Date of Patent: Nov. 17, 2026

(54) PROCESS FOR PRODUCTION OF LINEAR ALPHA OLEFINS WITH PARALLEL REACTORS

(71) Applicant: SABIC Global Technologies B.V., Bergen op Zoom (NL)

(72) Inventors: Shahid Azam, Riyadh (SA); Abdulrahman Ashri, Riyadh (SA); Abdulmajeed Mohammed Al-Hamdan, Riyadh (SA); Sebastiano Licciulli, Riyadh (SA); Ilia Korobkov, Thuwal (SA); Abdullah Saad Al-Dughaither, Riyadh (SA); Zaid Mohammed Binhazzaa, Riyadh (SA)

(73) Assignee: SABIC GLOBAL TECHNOLOGIES B. V., Bergen op Zoom (NL)

( * ) Notice: Subject to any disclaimer, the term of this patent is extended or adjusted under 35 U.S.C. 154(b) by 143 days.

(21) Appl. No.: 18/044,561

(22) PCT Filed: Sep. 2, 2021

(86) PCT No.: PCT/IB2021/058030
§ 371 (c)(1),
(2) Date: Mar. 9, 2023

(87) PCT Pub. No.: WO2022/053916
PCT Pub. Date: Mar. 17, 2022

(65) Prior Publication Data

US 2023/0331641 A1 Oct. 19, 2023

Related U.S. Application Data

(60) Provisional application No. 63/076,172, filed on Sep. 9, 2020.

(51) Int. Cl.
*C07C 2/08* (2006.01)
*B01J 19/24* (2006.01)

(52) U.S. Cl.
CPC ............. *C07C 2/08* (2013.01); *B01J 19/2445* (2013.01); *B01J 2219/00038* (2013.01); *B01J 2219/00103* (2013.01); *B01J 2219/00252* (2013.01)

(58) Field of Classification Search
CPC ... C07C 2/08; C07C 2/32; C07C 11/02; B01J 8/007; B01J 19/002; B01J 19/2445;
(Continued)

(56) References Cited

U.S. PATENT DOCUMENTS

| | | | | |
|---|---|---|---|---|
| 4,775,309 | A | 10/1988 | Hehl | |
| 7,129,304 | B1 * | 10/2006 | Small | B01J 31/143 526/171 |

(Continued)

FOREIGN PATENT DOCUMENTS

| | | | |
|---|---|---|---|
| WO | 2010024958 | A2 | 3/2010 |
| WO | 2012071644 | A1 | 6/2012 |
| WO | 2018233999 | A1 | 12/2018 |

*Primary Examiner* — In Suk C Bullock
*Assistant Examiner* — Jason Y Chong
(74) *Attorney, Agent, or Firm* — Womble Bond Dickinson (US) LLP

(57) ABSTRACT

Systems and methods for producing Linear Alpha Olefins are disclosed. The system includes two or more reaction units that are arranged in parallel. The system includes a cleaning unit configured to flush one or more of the reaction units that is off-stream while the remaining reaction units are on-stream for producing Linear Alpha Olefins.

13 Claims, 2 Drawing Sheets

(58) Field of Classification Search
CPC .... B01J 2219/00038; B01J 2219/00076; B01J 2219/00103; B01J 2219/00247; B01J 2219/00252
See application file for complete search history.

(56) References Cited

U.S. PATENT DOCUMENTS

| | | | | |
|---|---|---|---|---|
| 8,658,750 | B2 | 2/2014 | Lattner et al. | |
| 9,718,897 | B1 | 8/2017 | Burton et al. | |
| 9,856,184 | B2 | 1/2018 | Stochniol et al. | |
| 10,112,876 | B2 | 10/2018 | Azam et al. | |
| 10,370,307 | B2 | 8/2019 | Boutrot et al. | |
| 10,414,699 | B2 | 9/2019 | Bischof et al. | |
| 2008/0234443 | A1 | 9/2008 | Kiss et al. | |
| 2010/0056834 | A1 | 3/2010 | Phillion et al. | |
| 2010/0081842 | A1* | 4/2010 | Gao | B01J 31/188 585/511 |
| 2012/0029258 | A1* | 2/2012 | Wohl | B01J 31/143 585/527 |
| 2012/0142989 | A1 | 6/2012 | Jaber et al. | |
| 2014/0142360 | A1 | 5/2014 | Brown et al. | |
| 2016/0237000 | A1 | 8/2016 | Jaber et al. | |
| 2017/0081257 | A1* | 3/2017 | Kreischer | C07C 2/88 |
| 2017/0101354 | A1* | 4/2017 | Brown | C07C 2/36 |
| 2019/0002365 | A1* | 1/2019 | Patel | C07C 2/08 |
| 2019/0284109 | A1 | 9/2019 | Sujith et al. | |
| 2021/0107846 | A1 | 4/2021 | Augier et al. | |

* cited by examiner

PROCESS FOR PRODUCTION OF LINEAR ALPHA OLEFINS WITH PARALLEL REACTORS

CROSS-REFERENCE TO RELATED APPLICATIONS

This application is a 371 U.S. national stage application of International Application No. PCT/IB2021/058030, filed Sep. 2, 2021, which claims the benefit of priority of U.S. Provisional Application No. 63/076,172 filed Sep. 9, 2020, all of which are incorporated herein by reference in their entirety.

FIELD OF INVENTION

The present invention generally relates to systems and methods for oligomerization of olefins. More specifically, the present invention relates to systems and methods for producing linear alpha olefins (LAO) via oligomerization of ethylene.

BACKGROUND OF THE INVENTION

Linear Alpha Olefins (LAO) are important chemicals used as intermediates in various chemical processes. For instance, $C_4$ to $C_8$ LAOs are used as comonomers in the production of polyethylene. $C_4$ to $C_8$ LAOs can also be used for production of linear aldehyde as an intermediate for short-chain fatty acid and linear alcohols.

Conventionally, Linear Alpha Olefins can be produced via oligomerization of ethylene. However, there are several drawbacks associated with production of Linear Alpha Olefins using this method. First, oligomerization of ethylene inherently produces polymers, which form polymeric deposits in the oligomerization units, including reactors, heat exchangers, pipes, and pumps. The accumulated polymers on the surface of these devices and reactors can reduce heat transfer to or from the device and cause fouling. Thus, the oligomerization reactors have to be periodically shut down for cleaning of polymeric deposit, resulting in loss of production time and low production efficiency for Linear Alpha Olefins. Secondly, the oligomerization system, especially the reactor, is highly sensitive to the presence of moisture and oxygen, which further increases the polymer formation during the production process.

Overall, while systems and methods for producing Linear Alpha Olefins via oligomerization of ethylene exist, the need for improvements in this field persists in light of at least the aforementioned drawbacks for the conventional systems and methods.

BRIEF SUMMARY OF THE INVENTION

A solution to at least some of the above mentioned problems associated with systems and methods for producing LAO is discovered. The solution resides in a system and a method for producing LAO that includes two or more reaction units operated in parallel. Each of the reaction units can include a reactor, a heat exchanger, a pump, and optionally a polymer filter. This can be beneficial for at least avoiding shutting down the whole system when one or more reaction units are being cleaned to remove polymeric deposit, thus improving the production time and production efficiency for the LAO production system. Furthermore, the disclosed method can include passivating the reaction units of the LAO production system using an inert gas and a solvent and aluminum alkyl mixture, prior to flowing the feedstock into the oligomerization reactor, to remove moisture and oxygen from the reaction system, thereby reducing polymer formation during the LAO production process. Thus, the disclosed method is capable of reducing the frequency for cleaning the reaction units of the system, resulting in improved production efficiency. Moreover, the disclosed method can include adding an optimized amount of polymer inhibition additive into the reactors, thereby further reducing formation of polymer deposit in the LAO production system and improving LAO production efficiency. Therefore, the systems and methods of the present invention provide a technical solution to at least some problems associated with the conventional systems and methods for producing LAO.

Embodiments of the invention include a system for producing linear alpha olefins. The system comprises two or more reaction units configured to react ethylene, in the presence of the catalyst, to produce one or more linear alpha olefins. The two or more reaction units are operated in parallel. Each of the two or more reaction units comprises a reactor and a heat exchanger configured to cool at least a portion of an effluent stream from the reactor. The system comprises a cleaning unit in fluid communication with the two or more reaction units, and configured to remove at least some polymer deposit in the two or more reaction units. The cleaning unit is configured to remove polymer deposit from at least one of the reaction units while the remaining reaction units are on-stream for producing the linear alpha olefins.

Embodiments of the invention include a method for producing linear alpha olefins. The method comprises flowing a feed stream comprising ethylene into one or more reactors of one or more reaction units. Each reaction unit comprises a reactor, and a heat exchanger configured to cool at least a portion of an effluent stream from the reactor, and the reaction units are operated in parallel. The method comprises reacting, in the one or more reactors, the ethylene in the presence of a catalyst and optionally a solvent under reaction conditions sufficient to produce one or more linear alpha olefins. The method comprises recycling at least a portion of an effluent stream flowing from each of the one or more reactors back to the one or more reactors. The effluent stream comprises the one or more linear alpha olefins, unreacted ethylene, the catalyst, and optionally the solvent. The method comprises separating, in a separation unit, at least a portion of the effluent stream from each of the one or more reactors to produce an ethylene recycle stream comprising primarily ethylene, optionally a recycle solvent stream, and one or more product streams comprising linear alpha olefins.

Embodiments of the invention include a method for producing linear alpha olefins. The method comprises passivating the one or more reaction units of a linear alpha olefins production system by removing moisture and oxygen therefrom. Each reaction unit comprises a reactor, and a heat exchanger configured to cool at least a portion of an effluent stream from the reactor, and the reaction units are operated in parallel. The method comprises flowing a feed stream comprising ethylene into one or more reactors of one or more reaction units. The method comprises reacting, in the one or more reactors, the ethylene in the presence of a catalyst and optionally solvent under reaction conditions sufficient to produce one or more linear alpha olefins. The method comprises recycling at least a portion of an effluent stream flowing from each of the one or more reactors back to the one or more reactors. The effluent stream comprises the one or more linear alpha olefins, unreacted ethylene, optionally the solvent, and the catalyst. The method comprises separating, in a separation unit, at least a portion of the effluent stream from each of the one or more reactors to produce a recycle stream comprising primarily ethylene, optionally a recycle solvent stream, and one or more product streams comprising linear alpha olefins. The method comprises flushing at least one of the reaction units with a solvent to remove polymer deposits formed in the reaction unit during the reacting step while the remaining reaction units are on-stream for producing linear alpha olefins. The polymer is then removed from the flushing solvent, in a separation unit, to produce a clean flushing solvent that can be recycled to the cleaning unit.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol.%, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, LAO can be produced via oligomerization of ethylene. However, conventional processes for producing LAO have relatively low efficiency due to several factors. Since the oligomerization of ethylene inevitably produces polymers, polymer deposit is gradually formed in the reactor, the heat exchanger, the pipe, and/or the pump, resulting in fouling of the equipment of the LAO production system. Generally, the LAO production system has to be shut down in order to clean the polymer deposit therefrom, resulting in low production time (on-stream time). Additionally, the conventional LAO production system, due to frequent shut down, may ingress high concentrations of moisture and oxygen, which enhances polymer formation in the LAO production system. The present invention provides a solution to at least some of these problems. The solution is premised on a system and a method that includes two or more reaction units operated in parallel such that when one or more reaction units are taken off-stream, other reaction units are on-stream for producing LAO, thereby mitigating the reduced production time for conventional systems and methods. The disclosed systems and methods further include passivating the reaction units via purging with an inert gas and circulating a solvent and aluminum alkyl mixture through the reaction units prior to flowing the feed stream therein, thereby significantly reducing the moisture and oxygen content in the reaction units. Moreover, the disclosed method includes adding a polymer inhibition additive into the reaction units to inhibit polymer formation during the LAO production process, thereby increasing the LAO production efficiency and reducing the frequency for cleaning polymer deposit. These and other non-limiting aspects of the present invention are discussed in further detail in the following sections.

A. System for Producing Linear Alpha Olefins

Figure 1:
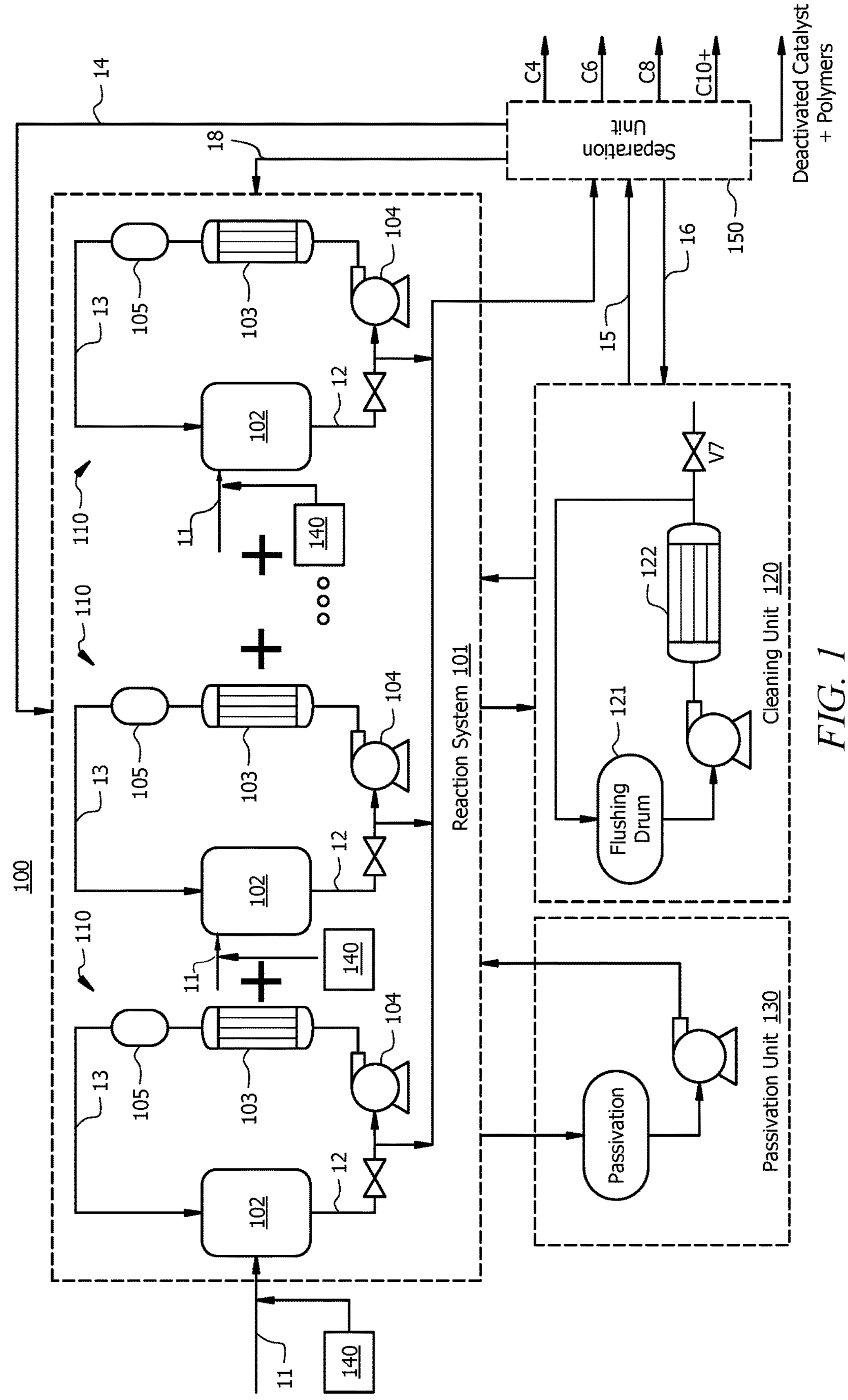
FIG. 1 shows a system for producing linear alpha olefins, according to embodiments of the invention.

In embodiments of the invention, the system for producing Linear Alpha Olefins (LAO) comprises a reaction system, a cleaning unit, a separation unit, and a passivation unit. With reference to FIG. 1, a schematic diagram is shown for system 100, which is used for producing LAO via ethylene oligomerization.

According to embodiments of the invention, system 100 includes reaction system 101 configured to receive feed stream 11 comprising ethylene and react ethylene to produce one or more LAO. In embodiments of the invention, reaction system 101 includes two or more reaction units 110 arranged in parallel. In embodiments of the invention, feed stream 11 may further include a solvent, a polymer inhibition additive, and a catalyst configured to catalyze oligomerization of ethylene. The catalyst may comprises any catalyst known in the art that is capable of catalyzing ethylene oligomerization. In embodiments of the invention, the catalyst includes a metal compound, a ligand, optionally a modifier including quaternary ammonium salts, quaternary phophonium solvents, sulfonates, or combinations thereof, an aluminum alkyl as a co-catalyst, or combinations thereof. The catalyst may further include a solvent including aromatics, paraffinics, olefinics, which can include decaline, toluene, hexane, heptane, octane, xylene, iso-pentane, cyclohexane, or combinations thereof. The metal compound can include chromium. Exemplary metal compounds can include $CrCl_3$ (tetrahydrofurane)3, Cr(III)acetylacetonate, Cr(III) octanoate, Cr-hexacarbonyl, Cr(III)-2-ethylhexanoate, (benzene)tricarbonyl-chromium, or combinations thereof. The aluminum alkyl in the catalyst may be capable of scavenging moisture, oxygen, and/or other impurities. Exemplary aluminum alkyl co-catalysts can include trimethylaluminum, triethylaluminum, triisopropylaluminum, triisobutylaluminum, ethylaluminumsesquichloride, diethylaluminum chloride, ethylaluminumdichloride, methylaluminoxane [MAO], modified methylaluminoxane [MMAO], or combinations thereof. Exemplary ligands can include a PNPNH backbone-based organic compound where each P and N may have independently aromatic, aliphatic, linear or cyclic substituents and such substituents may contain other heteroatoms including N,S,P such as (Ph)2P—N(i-Pr)—P(Ph)—N(i-Pr)—H; alternatively the ligand could be an NPNPN backbone based organic compound where each P and N have independently aromatic, aliphatic, linear or cyclic substituents and the substituents contain other heteroatoms including N,S,P such as (n-Bu)(Me)N—P(Cy)-N(Me)—P(Cy)-N(n-Bu)(Me), where Cy is a cyclohexyl group, Me is methyl group, and n-Bu is a normal butyl group.

In embodiments of the invention, each reaction unit 110 comprises reactor 102 configured to react ethylene in the presence of a catalyst to form one or more LAO in effluent stream 12. In embodiments of the invention, reactor 102 comprises a liquid-gas phase reactor. Each reaction unit 110 may further include heat exchanger 103 in fluid communication with an outlet of reactor 102. Heat exchanger 103 is configured to cool a portion of effluent stream 12 to form recycle effluent stream 13. In embodiments of the invention, effluent stream 12 further comprises the catalyst, unreacted ethylene, optionally the solvent (from feed stream 11), polymers, or combinations thereof.

In embodiments of the invention, each reaction unit 110 further comprises pump 104 configured to drive at least a portion of effluent stream 12 into heat exchanger 103. Each reaction unit 110 may further comprise filter 105 in fluid communication with heat exchanger 103. Filter 105 may be configured to remove polymers from recycle effluent stream 13.

According to embodiments of the invention, system 100 further comprises cleaning unit 120 in fluid communication with reaction system 101. Cleaning unit 120 may be in fluid communication with each reaction unit 110 of reaction system 101. In certain embodiments of the invention, each reaction unit 110 has a different cleaning unit 120, or different sets of reaction units 110 have different cleaning units 120. In embodiments of the invention, cleaning unit 120 is configured to flush, using a solvent, one or more reaction units 110 to remove polymer deposits therefrom. At least a portion of the solvent flushing through one or more reaction units 110 may be flowed into a separation unit, which is configured to separate dissolved polymer in the solvent to produce regenerated solvent. The regenerated solvent may be flowed back to cleaning unit 120. In embodiments of the invention, cleaning unit 120 comprises flushing drum 121 configured to store the solvent, and heat exchanger 122 configured to heat or cool the solvent. Exemplary solvents used in cleaning unit 120 can include aromatics, paraffinics, olefinics, which can include decaline, toluene, hexane, heptane, octane, xylene, iso-pentane, cyclohexane, or combinations thereof. In embodiments of the invention, reaction system 101 and cleaning unit 120 are configured to be operated such that one or more off-stream reaction units 110 are being flushed while the remaining reaction units 110 of reaction system 101 are on-stream for producing LAO.

According to embodiments of the invention, system 100 comprises passivation unit 130 in fluid communication with reaction system 101. In embodiments of the invention, passivation unit 130 is configured to remove moisture and/or oxygen from reaction units 110. Passivation unit 130 includes an inert gas module configured to provide one or more reaction units 110 with an inert gas to reduce moisture and oxygen concentration in reaction units 110 to a first level. The inert gas may include nitrogen, helium, argon, or combinations thereof. Passivation unit 130 may further include a solvent module configured to circulate a mixture comprising a solvent and an aluminum alkyl through each of two or more reaction units 110 to reduce moisture and oxygen concentration in reaction units 110 to a second level. In embodiments of the invention, the first level is 500 to 1000 ppm and the second level is about 1 to 10 ppm.

According to embodiments of the invention, reaction system 101 comprises polymer inhibition additive unit 140 configured to add one or more polymer inhibition additives into reactor 102 of each of reaction units 110. Exemplary polymer inhibition additive can include hydrogen. In embodiments of the invention, the polymer inhibition additive can be directly added to reactor 102. Alternatively or additionally, the polymer inhibition additive can be mixed in feed stream 11. Alternatively, or additionally, the polymer inhibition additive can be mixed with the catalyst.

According to embodiments of the invention, reaction system 101 comprises separation unit 150 in fluid communication with an outlet of each reactor 102 such that at least a portion of effluent stream 12 from one or more of reactors 102 flows from reactor 102 to separation unit 150. In embodiments of the invention, the at least a portion of effluent stream 12, prior to being flowed to separation unit 150, is mixed with a catalyst deactivating agent configured to deactivate the catalyst in at least a portion of effluent stream 12. In embodiments of the invention, the deactivating agent comprises alcohol, amines, water, caustics, air, or combinations thereof.

In embodiments of the invention, separation unit 150 is configured to separate at least a portion of effluent stream 12 from two or more reactors 102 to produce one or more product streams comprising LAO, a recycle stream of solvents, and ethylene recycle stream 14 comprising primarily ethylene. In embodiments of the invention, separation unit 150 includes a series of distillation columns. The distillation columns of separation unit 150 can include a $C_2$ separation column configured to separate a portion of effluent stream 12 to form ethylene recycle stream 14 and a $C_3$+ stream. Separation unit 150 may comprise a $C_6$ separation column configured to separate the $C_3$+ stream to form a 1-hexene stream comprising primarily 1-hexene, and a $C_7$+ stream. Separation unit 150 may comprise a $C_7$ separation column configured to separate the $C_7$+ stream to produce a $C_7$ stream to form solvent recycle stream 18 and $C_8$+ stream. Separation unit 150 may comprise a $C_8$ separation column configured to separate $C_8$+ stream to form a 1-octene stream and $C_8$+ stream. Separation unit 150 may further comprise a cleaning solvent separation column configured to separate the $C_8$+ stream to form a cleaning solvent stream and a heavies stream. In embodiments of the invention, the cleaning solvent stream can be recycled as the solvent for the cleaning unit. In embodiments of the invention, the heavies stream can comprise the catalyst, the deactivating agent, polymers, or combinations thereof. In embodiments of the invention, separation unit 150 is further configured to separate polymers from solvent-polymer stream 15 from cleaning device 120 to produce regenerated solvent stream 16 comprising regenerated solvent. Regenerated solvent stream 16 may be flowed back to cleaning device 120.

B. Method for Producing Oligomers

Figure 2:
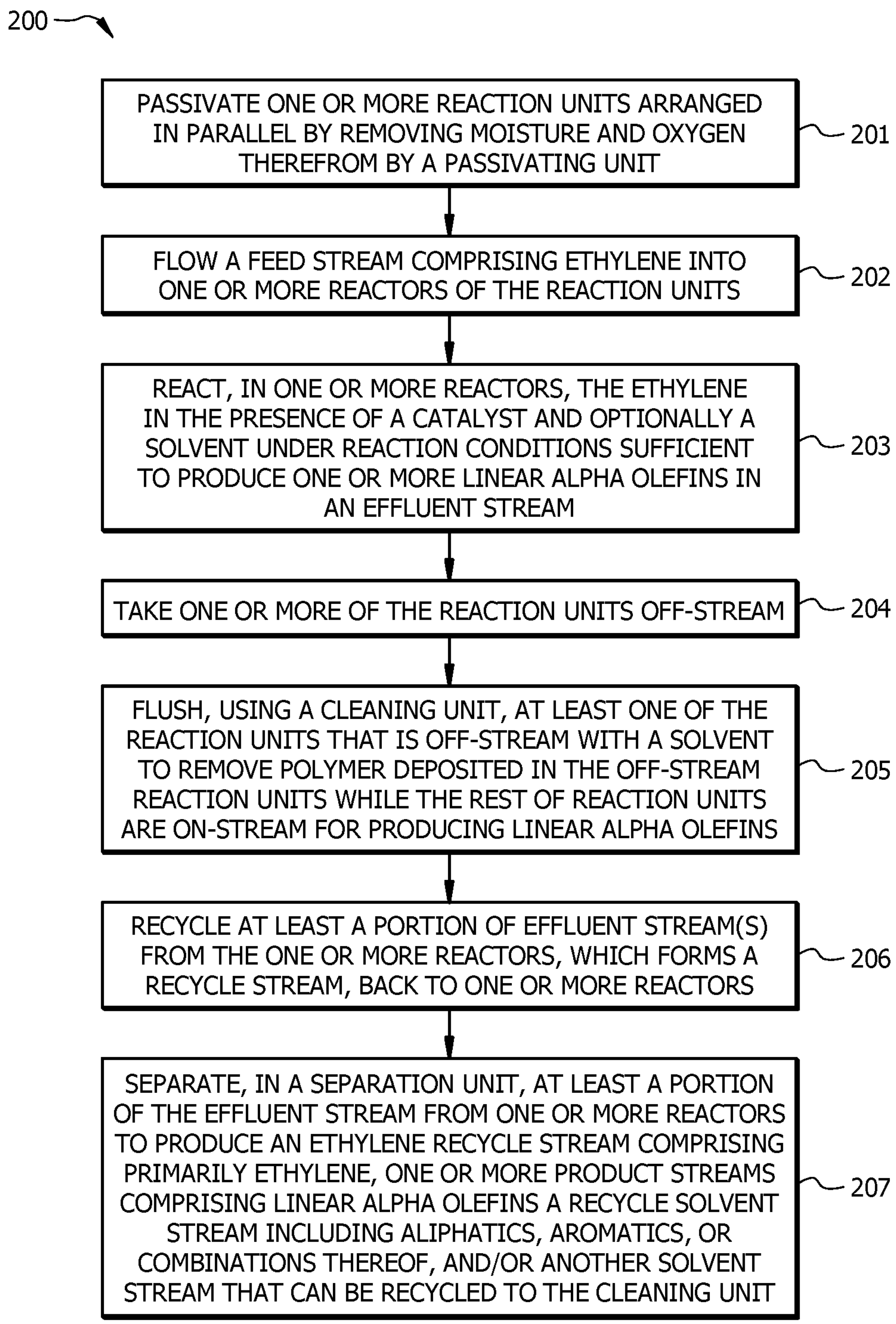
FIG. 2 shows a method of producing linear alpha olefins, according to embodiments of the invention.

Methods of producing Linear Alpha Olefins have been discovered. As shown in FIG. 2, embodiments of the invention include method 200 for producing LAO, with improved production efficiency compared to conventional methods. Method 200 may be implemented by system 100 as shown in FIG. 1 and described above.

According to embodiments of the invention, as shown in block 201, method 200 includes passivating, using passivation unit 130, one or more reaction units 110 by removing moisture and oxygen therefrom. In embodiments of the invention, passivating at block 201 can include purging one or more reaction units 110 with an inert gas to reduce a concentration of the moisture and oxygen in reaction units 110 to a first level. The inert gas can include nitrogen, helium, argon, or combinations thereof. In embodiments of the invention, at block 201, the purging is conducted at an inert gas temperature above room temperature, preferably a temperature of 20 to 300° C. and all ranges and values there between. The first level of the concentration of the moisture and oxygen may be in a range of 500 to 1000 ppm and all ranges values there between including ranges of 500 to 600 ppm, 600 to 700 ppm, 700 to 800 ppm, 800 to 900 ppm, and 900 to 1000 ppm.

In embodiments of the invention, passivating at block 201 can further include circulating a solvent and aluminum alkyl mixture through one or more reactors 102 to further reduce the concentration of the moisture and oxygen in reaction units 110 to a second level. In embodiments, the solvent and aluminum alkyl mixture comprises 0.0001 to 7 wt. % aluminum alkyl and all ranges and values there between. The second level of the concentration of the moisture and oxygen in reaction units 110 may be in a range of 1 to 10 ppm and all ranges and values there between. The circulating at block 201 may be conducted at a temperature of the solvent aluminum alkyl in a range of 20 to 150° C. and all ranges and values there between including ranges of 20 to 30° C., 30 to 40° C., 40 to 50° C., 50 to 60° C., 60 to 70° C., 70 to 80° C., 80 to 90° C., 90 to 100° C., 100 to 110° C., 110 to 120° C., 120 to 130° C., 130 to 140° C., and 140 to 150° C.

According to embodiments of the invention, as shown in block 202, method 200 includes flowing feed stream 11 comprising ethylene into one or more reactors 102 of two or more reaction units 110. As shown in system 100, each reaction unit 110 comprises reactor 102. Two or more reaction units 110 are operated in parallel. In embodiments of the invention, feed stream 11 comprising ethylene, the catalyst and the solvent are introduced into each reactor 102 and effluent stream 12 from each reactor 102 is combined together before sending to separation unit 150. In embodiments of the invention, feed stream 11 comprises the catalyst for oligomerization of ethylene. The catalyst includes the metal compound, the ligand, the modifier, the solvent, and the aluminum alkyl co-catalyst. In embodiments of the invention, feed stream 11 can be produced by a jet mixer for mixing ethylene, the catalyst, and/or the polymer inhibition agent to form feed stream 11. In embodiments of the invention, the polymer inhibition agent can be added directly into reactor 102 of each of two or more reaction units 110, configured to reduce the production of polymers in reaction units 110. The polymer inhibition agent can include hydrogen. The hydrogen concentration in reactor 102 may be in a range of 0 to 12 wt. % and all ranges and values there between including ranges of 0 to 2 wt. %, 2 to 4 wt. %, 4 to 6 wt. %, 6 to 8 wt. %, 8 to 10 wt. %, and 10 to 12 wt. %.

According to embodiments of the invention, as shown in block 203, method 200 includes reacting, in one or more reactors 102, the ethylene in the presence of the catalyst and optionally a solvent under reaction conditions sufficient to produce one or more linear alpha olefins in effluent stream 12. In embodiments of the invention, the reaction conditions can include a reaction temperature in a range of 20 to 200° C. and all ranges and values there between including ranges of 20 to 40° C., 40 to 60° C., 60 to 80° C., 80 to 100° C., 100 to 120° C., 120 to 140° C., 140 to 160° C., 160 to 180° C., and 180 to 200° C. The reaction conditions can include a reaction pressure of 5 to 100 bar and all ranges and values there between. In embodiments of the invention, the linear alpha olefins produced at block 203 include 1-butene, 1-hexene, 1-octene, $C_{10+}$, or combinations thereof. In embodiments of the invention, effluent stream 12 comprises 0.1 to 75 wt. % 1-hexene, and 0.1 to 75 wt. % 1-octene. Effluent stream 12 may further comprise ethylene, polymers, the catalyst, traces of butenes, $C_{10}$+, or combinations thereof.

According to embodiments, as shown in block 204, method 200 includes taking one or more reaction units 110 off-stream. According to embodiments of the invention, as shown in block 205, method 200 includes flushing, using cleaning unit 120, at least one of reaction units 110 that is off-stream with a solvent to remove polymer deposited in reaction units 110 while the remaining reaction units 110 are on-stream for producing linear alpha olefins. In embodiments of the invention, the solvent includes a flushing medium. In embodiments of the invention, the flushing at block 205 includes flushing with the solvent from upstream of pump 104 through heat exchanger 103, and drawing off the solvent back to the flushing drum 121 of cleaning unit 120. Flushing at block 205 further includes flushing reactor 102 with the solvent via a jet mixer and via an outlet of reactor 102 simultaneously, and drawing the solvent from reactor 102 bottom to flushing drum 121 of cleaning unit 120. In embodiments of the invention, at least a portion of the solvent drawn from reactor 102, pump 104 and/or heat exchanger 103 are separated in separation unit 150 to produce regenerated solvent stream 16.

According to embodiments of the invention, as shown in block 206, method 200 includes recycling at least a portion of effluent stream 12, which forms recycle stream 13, back to one or more reactors 102. In embodiments of the invention, recycle stream 13 may be cooled in heat exchanger 103 before being flowed back to reactors 102. Recycle stream 13 may be cooled by 1 to 15° C. from reaction temperature and all ranges and values there between including ranges of 1 to 3° C., 3 to 6° C., 6 to 9° C., 9 to 12° C., and 12 to 15° C.

According to embodiments of the invention, as shown in block 207, method 200 includes separating, in separation unit 120, at least a portion of effluent stream 12 from each of one or more reactors 102 to produce ethylene recycle stream 14 comprising primarily ethylene, one or more product streams comprising LAO, a recycle solvent stream including aliphatics, aromatics, or combinations thereof, and/or additionally another solvent stream recycled to cleaning unit 120. In embodiments of the invention, prior to block 207, a catalyst deactivating agent is added into effluent stream 12 to deactivate the catalyst. The deactivating agent may include alcohol, amines, water, caustic, air, or combinations thereof. Examples of the alcohol include decanol and/or 2-ethylhexanol.

Although embodiments of the present invention have been described with reference to blocks of FIG. 2 should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

In the context of the present invention, at least the following 20 embodiments are described. Embodiment 1 is a system for producing linear alpha olefins. The system includes two or more reaction units configured to react ethylene, in the presence of a catalyst, and optionally a solvent to produce one or more linear alpha olefins, wherein the two or more reaction units are arranged in parallel, and each of the two or more reaction units includes a reactor. The system further includes a cleaning unit configured for communication with the two or more reaction units, and to flush polymeric deposits from at least one off-stream reaction unit of the two or more reaction units while the remaining reaction units are on-stream for producing the linear alpha olefins. Embodiment 2 is the system of embodiment 1, wherein each of the reaction units further includes a heat exchanger configured to cool at least a portion of an effluent stream from the reactor, a pump, and/or a polymer removal filter in fluid communication with the reactor. Embodiment 3 is the system of either of embodiments 1 or 2, further including a passivation unit in fluid communication with each of the reaction units, configured to remove moisture and oxygen from each of the reaction units. Embodiment 4 is the system of embodiment 3, wherein the passivation unit includes an inert gas module configured to purge each of the reaction units with an inert gas to reduce the moisture and oxygen, and a solvent module configured to circulate a mixture containing a solvent and an aluminum alkyl through each of the two or more reaction units. Embodiment 5 is the system of any of embodiments 1 to 4, wherein a catalyst deactivating agent is added to a portion of effluent stream to deactivate the catalyst and form a separation feed stream, and the system further includes a separation unit configured to separate at least a portion of an effluent stream from each reactor of each of the two or more reaction units to produce one or more of: (a) a recycle ethylene stream containing primarily ethylene, (b) one or more product streams containing one or more linear alpha olefins, (c) a solvent recycle stream containing a solvent used as a process diluent and (d) a heavies stream containing the catalyst, polymers, and/or the catalyst deactivating agent.

Embodiment 6 is a method for producing linear alpha olefins. The method includes flowing a feed stream containing ethylene into one or more reactors of two or more reaction units, wherein each reaction unit includes a reactor, and the two or more reaction units are operated in parallel. The method further includes reacting, in the one or more reactors, the ethylene in the presence of a catalyst and optionally a solvent under reaction conditions sufficient to produce one or more linear alpha olefins. Embodiment 7 is the method of embodiment 6, wherein the reacting further produces polymers and at least a portion of the polymers is deposited in the reaction units, wherein the method further includes flushing at least one of the reaction units with a solvent to remove the polymer deposited in the reaction units while the remaining reaction units are on-stream for producing linear alpha olefins. Embodiment 8 is the method of embodiment 7, wherein the solvent includes aromatics, paraffinics, and/or olefinics solvents containing decaline, toluene, hexane, heptane, octane, xylene, iso-pentane, cyclohexane, or combinations thereof. Embodiment 9 is the method of any of embodiments 6 to 8, wherein the one or more reactors are liquid-gas phase reactors, and the feed stream further contains the catalyst, a solvent, a polymer inhibition additive, or combinations thereof. Embodiment 10 is the method of embodiment 9, wherein the catalyst contains a metal source, an aluminum alkyl, optionally a modifier, and a ligand. Embodiment 11 is the method of embodiment 9, wherein the metal source includes a chromium containing species containing $CrCl_3$(tetrahydrofurane)3, Cr(III)acetylacetonate, Cr(III)octanoate, Cr-hexacarbonyl, Cr(III)-2-ethylhexanoate, (benzene)tricarbonylchromium, or combinations thereof, wherein the aluminum alkyl contains trimethylaluminum, triethylaluminum, triisopropylaluminum, triisobutylaluminum, ethylaluminumsesquichloride, diethylaluminum chloride, ethylaluminumdichloride, methylaluminoxane [MAO], modified methylaluminoxane [MMAO], or combinations thereof, wherein the modifier contains quaternary ammonium salts, quaternary phophonium salts, sulfonates, or combinations thereof, and wherein the ligand contains a PNPNH backbone based organic compound where each P and N may have independently aromatic, aliphatic, linear or cyclic substituents and such substituents maybe containing other heteroatoms including N,S,P such as (Ph)2P—N(i-Pr)—P(Ph)—N(i-Pr)—H; alternatively the ligand may comprise an NPNPN backbone based organic compound where each P and N have independently aromatic, aliphatic, linear or cyclic substituents and the substituents contain other heteroatoms including N,S,P such as (n-Bu)(Me)N—P(Cy)-N(Me)—P(Cy)-N(n-Bu)(Me), where Cy is a cyclohexyl group, Me is a methyl group, and n-Bu is a normal butyl group. Embodiment 12 is the method of any of embodiments 6 to 11, further including flowing polymer inhibition additive including hydrogen to the one or more reactors. Embodiment 13 is the method of embodiment 12, wherein the hydrogen is mixed in the feed stream or injected directly to the reactor. Embodiment 14 is the method of any of embodiments 6 to 13, wherein each of the one or more reaction units further includes a heat exchanger configured to cool at least a portion of an effluent stream from the reactor, and a pump. Embodiment 15 is the method of any of embodiments 6 to 14, further including, prior to flowing the feed stream to the reactors, passivating the one or more reaction units by removing moisture and oxygen therefrom. Embodiment 16 is the method of embodiment 15, wherein the passivating includes purging the one or more reaction units with an inert gas to reduce a concentration of the moisture and the oxygen in the reaction units to a first level. The method further includes circulating a solvent and aluminum alkyl mixture through the one or more reaction units to further reduce the moisture and oxygen in the reaction units to a second level. Embodiment 17 is the method of embodiment 16, wherein the first level is 500 to 1000 ppm, and the second level is 1 ppm to 10 ppm, and wherein the inert gas is at a temperature of 20 to 300° C. and the solvent and aluminum alkyl mixture is at a temperature of 20 to 150° C. Embodiment 18 is the method of any of embodiments 6 to 16, further including recycling at least a portion of an effluent stream from each of the one or more reactors back to the one or more reactors, wherein the effluent stream contains the one or more linear alpha olefins, unreacted ethylene, optionally a solvent, and the catalyst. The method further includes deactivating the catalyst of at least a portion of the effluent stream from each reaction unit to produce a separation feed stream. The method still further includes separating, in a separation unit, the separation feed stream to produce an ethylene recycle stream containing primarily ethylene, a solvent recycle stream, and one or more product streams containing one or more linear alpha olefins. Embodiment 19 is the method of any of embodiments 6 to 18, wherein the reaction conditions include a reaction temperature of 20 to 200° C. and a reaction pressure of 5 to 100 bar. Embodiment 20 is the method of embodiment 19, wherein the effluent stream contains 0.1 to 75 wt. % 1-hexene and/or 0.1 to 75 wt. % 1-octene.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for producing linear alpha olefins, the method comprising:

flowing a feed stream comprising ethylene into one or more reactors of two or more reaction units, wherein each reaction unit comprises a reactor, and the two or more reaction units are operated in parallel, each reaction unit of the two or more reaction units having a cleaning unit comprising a flushing drum;

reacting, in the one or more reactors, the ethylene in the presence of a catalyst and a solvent under reaction conditions sufficient to produce an effluent stream comprising one or more linear alpha olefins, unreacted ethylene, solvent, and the catalyst;

wherein the reacting further produces polymers and at least a portion of the polymers is deposited in the reaction units;

prior to flowing the feed stream to the reactors, passivating the one or more reaction units by removing moisture and oxygen therefrom;

flushing at least one of the reaction units with a solvent from the flushing drum of the cleaning unit of the at least one of the reaction units to remove the polymer deposited in the reaction units while the remaining reaction units are on-stream for producing linear alpha olefins;

returning the solvent back to the flushing drum from the at least one of the reaction units after said flushing;

treating at least a portion of the solvent from the flushing drum in a separation unit to remove polymer and produce a regenerated solvent;

recycling the regenerated solvent back to the flushing drum from the separation unit for reuse as a flushing solvent;

treating the effluent stream in the separation unit to produce a plurality of effluent streams from the separation unit including at least one linear alpha olefin product stream and a cleaning solvent stream; and transferring the cleaning solvent stream to the flushing drum for use as a flushing solvent.

2. The method of claim 1, wherein flushing at least one of the reaction units with a solvent includes flushing with aromatics, paraffinics, and/or olefinics solvents comprising decaline, toluene, hexane, heptane, octane, xylene, isopentane, cyclohexane, or combinations thereof.

3. The method of claim 1, wherein the one or more reactors are liquid-gas phase reactors, and the feed stream further comprises the catalyst, a solvent, a polymer inhibition additive, or combinations thereof.

4. The method of claim 3, wherein the catalyst comprises a metal source, an aluminum alkyl, optionally a modifier, and a ligand.

5. The method of claim 4, wherein the metal source comprises a chromium containing species comprising $CrCl_3$ (tetrahydrofurane)$_3$, Cr(III) acetylacetonate, Cr(III) octanoate, Cr-hexacarbonyl, Cr(III)-2-ethylhexanoate, (benzene) tricarbonyl-chromium, or combinations thereof; wherein the aluminum alkyl comprises trimethylaluminum, triethylaluminum, triisopropylaluminum, triisobutylaluminum, ethylaluminumsesquichloride, diethylaluminum chloride, ethylaluminumdichloride, methylaluminoxane [MAO], modified methylaluminoxane [MMAO], or combinations thereof; wherein the modifier comprises quaternary ammonium salts, quaternary phosphonium salts, sulfonates, or combinations thereof; and wherein the ligand comprises a PNPNH backbone based organic compound where each P and N have independently aromatic, aliphatic, linear or cyclic substituents and such substituents optionally contain heteroatoms including N, S, and P; alternatively the ligand comprises an NPNPN backbone based organic compound where each P and N have independently aromatic, aliphatic, linear or cyclic substituents and the substituents optionally contain heteroatoms including N,S, and P.

6. The method of claim 1, further comprising flowing a polymer inhibition additive including hydrogen to the one or more reactors.

7. The method of claim 6, wherein the hydrogen is mixed in the feed stream or injected directly to the reactor.

8. The method of claim 1, wherein each of the one or more reaction units further comprises a heat exchanger configured to cool at least a portion of an effluent stream from the reactor, and a pump.

9. The method of claim 1, wherein the passivating comprises:

purging the one or more reaction units with an inert gas to reduce a concentration of the moisture and the oxygen in the reaction units to a first level; and circulating a solvent and aluminum alkyl mixture through the one or more reaction units to further reduce the moisture and oxygen in the reaction units to a second level.

10. The method of claim 9, wherein the first level is 500 to 1000 ppm, and the second level is 1 ppm to 10 ppm, and wherein the inert gas is at a temperature of 20 to 300° C. and the solvent and aluminum alkyl mixture is at a temperature of 20 to 150° C.

11. The method of claim 1, further comprising:

recycling at least a portion of the effluent stream from each of the one or more reactors back to the one or more reactors;

deactivating the catalyst of at least a portion of the effluent stream from each reaction unit to produce a separation feed stream; and separating, in the separation unit, the separation feed stream to produce an ethylene recycle stream comprising primarily ethylene, a solvent recycle stream, and one or more product streams comprising one or more linear alpha olefins.

12. The method of claim 1, wherein the reaction conditions include a reaction temperature of 20 to 200° C. and a reaction pressure of 5 to 100 bar.

13. The method of claim 12, wherein the effluent stream comprises 0.1 to 75 wt. % 1-hexene and/or 0.1 to 75 wt. % 1-octene.

* * * * *